(12) United States Patent
Fischvogt et al.

(10) Patent No.: US 10,888,309 B2
(45) Date of Patent: Jan. 12, 2021

(54) SURGICAL FASTENER DEVICES WITH GEOMETRIC TUBES

(71) Applicant: Covidien LP, Mansfield, MA (US)

(72) Inventors: Gregory Fischvogt, Denver, CO (US); Kevin Sniffin, Roxbury, CT (US); Kevin Beaulieu, Belchertown, MA (US); Brian Laird, Granby, CT (US)

(73) Assignee: COVIDIEN LP, Mansfield, MA (US)

( * ) Notice: Subject to any disclaimer, the term of this patent is extended or adjusted under 35 U.S.C. 154(b) by 206 days.

(21) Appl. No.: 15/838,669

(22) Filed: Dec. 12, 2017

(65) Prior Publication Data

US 2018/0214144 A1 Aug. 2, 2018

Related U.S. Application Data

(60) Provisional application No. 62/452,398, filed on Jan. 31, 2017.

(51) Int. Cl.
*A61B 17/04* (2006.01)
*A61B 17/00* (2006.01)
*A61B 17/064* (2006.01)
*A61B 17/128* (2006.01)
*A61B 17/068* (2006.01)

(52) U.S. Cl.
CPC ...... *A61B 17/0401* (2013.01); *A61B 17/0057* (2013.01); *A61B 17/064* (2013.01); *A61B 17/1285* (2013.01); *A61B 17/068* (2013.01); *A61B 2017/00349* (2013.01)

(58) Field of Classification Search
CPC ............ A61B 17/064; A61B 2017/064; A61B 2017/0647; A61B 2017/0648; A61B 2017/0649; A61M 25/005; A61M 25/0052; A61M 25/0053; A61M 25/0054; A61M 2025/0059; A61M 2025/006; A61F 2002/0072
USPC ........................................................ 606/139
See application file for complete search history.

(56) References Cited

U.S. PATENT DOCUMENTS

| 3,596,528 A | 8/1971 | Dittrich et al. |
| 3,866,510 A | 2/1975 | Eibes et al. |
| 4,350,491 A | 9/1982 | Steuer |

(Continued)

FOREIGN PATENT DOCUMENTS

| EP | 0374088 A1 | 6/1990 |
| EP | 1721575 A2 | 11/2006 |

(Continued)

OTHER PUBLICATIONS

Extended European Search Report issued in corresponding European Application No. 18154121.0 dated Oct. 19, 2018.

(Continued)

*Primary Examiner* — Martin T Ton
(74) *Attorney, Agent, or Firm* — Carter, DeLuca & Farrell LLP

(57) ABSTRACT

An end effector for a surgical fastening device includes a fastener and a tube defining a longitudinal axis. The tube includes an outer surface and an inner surface. The inner surface defines a lumen that extends along the longitudinal axis. The tube defines depressions that may be arranged helically about the tube along the longitudinal axis. The end effector may include one or more ribs extending along the tube.

19 Claims, 10 Drawing Sheets

(56) References Cited

U.S. PATENT DOCUMENTS

| | | |
|---|---|---|
| 4,730,726 A | 3/1988 | Holzwarth |
| 4,884,572 A | 12/1989 | Bays et al. |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,472 A * | 10/1996 | Gipperich ............ F16L 9/06 138/121 |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |

(56) References Cited

U.S. PATENT DOCUMENTS

| | | |
|---|---|---|
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2 | 10/2017 | Sniffin et al. |
| 9,788,833 B2 | 10/2017 | Zergiebel et al. |
| 2003/0009441 A1 | 1/2003 | Holsten et al. |
| 2004/0092937 A1 | 5/2004 | Criscuolo et al. |
| 2005/0070844 A1* | 3/2005 | Chow ............... A61M 25/0012 604/95.04 |
| 2005/0187613 A1* | 8/2005 | Bolduc ............... A61F 2/07 623/1.23 |
| 2005/0222665 A1 | 10/2005 | Aranyi |
| 2006/0129152 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0097523 A1* | 4/2008 | Bolduc ............... A61B 17/064 606/219 |
| 2008/0312687 A1 | 12/2008 | Blier |
| 2009/0112234 A1 | 4/2009 | Crainich et al. |
| 2009/0118776 A1 | 5/2009 | Kelsch et al. |
| 2010/0270354 A1 | 10/2010 | Rimer et al. |
| 2011/0022065 A1 | 1/2011 | Shipp |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2014/0005678 A1 | 1/2014 | Shelton, IV et al. |
| 2014/0014707 A1 | 1/2014 | Onukuri et al. |
| 2014/0200587 A1 | 7/2014 | Pompee et al. |
| 2014/0236196 A1 | 8/2014 | Colesanti et al. |
| 2014/0243855 A1 | 8/2014 | Sholev et al. |
| 2014/0276967 A1 | 9/2014 | Fischvogt et al. |
| 2015/0005748 A1 | 1/2015 | Sniffin et al. |
| 2015/0032130 A1 | 1/2015 | Russo |
| 2015/0133970 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0074034 A1 | 3/2016 | Shipp |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniftin et al. |
| 2017/0035567 A1* | 2/2017 | Duffy ............... A61F 2/966 |

FOREIGN PATENT DOCUMENTS

| | | |
|---|---|---|
| EP | 2528518 A2 | 12/2012 |
| JP | 09149906 | 6/1997 |
| WO | 2013046115 A1 | 4/2013 |

OTHER PUBLICATIONS

Extended European Search Report corresponding to EP 14 15 8946.5, completed Jun. 20, 2014 and dated Jul. 8, 2014;(9 pp).

Extended European Search Report corresponding to EP 14 17 8107.0, completed Nov. 24, 2014 and dated Dec. 3, 2014; (5 pp).

Extended European Search Report corresponding to EP 14 17 4656.0, completed Jan. 16, 2015 and dated Jan. 26, 2015; (7 pp).

Extended European Search Report corresponding to EP 14 18 4907.5, completed Jan. 12, 2015 and dated Jan. 27, 2015; (9 pp).

(56) References Cited

OTHER PUBLICATIONS

EP Search Report corresponding to EP 14 18 1900.3, completed Mar. 31, 2015 and dated Apr. 9, 2015; 7pp.
Extended European Search Report corresponding to counterpart application EP 14 19 7885.8 dated Apr. 30, 2015; 9pp.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
European Search Report corresponding to EP No. 10 01 2659.8, completed Dec. 21, 2010; dated Jan. 3, 2011; 3 pages.
European Search Report corresponding to EP No. 10 01 2646.5, completed Feb. 11, 2011; dated Feb. 22, 2011.
Extended European Search Report corresponding to Int'l Application No. EP 14 15 1663.3 dated Jun. 7, 2016.
Supplementary European Search Report dated Feb. 2, 2017 in corresponding European Patent Application No. 14817036, 8 pages.
European Search Report dated May 10, 2017 in corresponding European Patent Application No. 17157259.7, 12 pages.

* cited by examiner

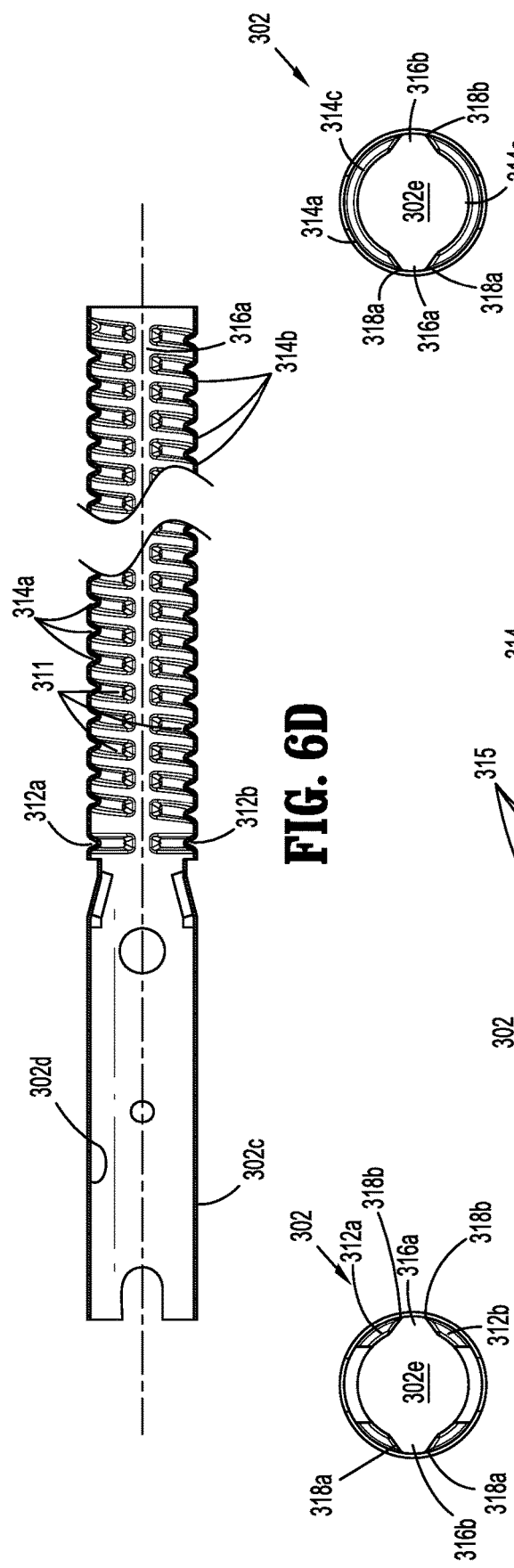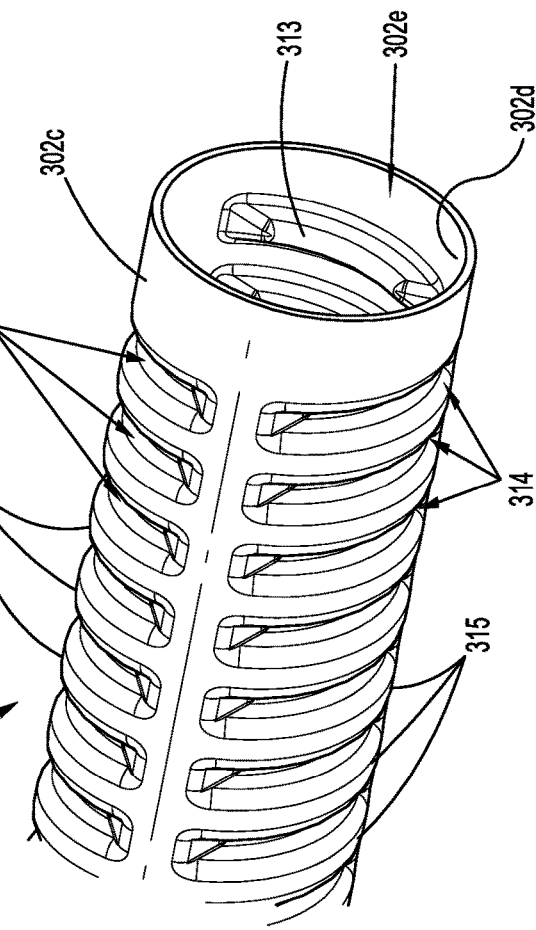

SURGICAL FASTENER DEVICES WITH GEOMETRIC TUBES

CROSS-REFERENCE TO RELATED APPLICATIONS

This application claims the benefit of and priority to U.S. Provisional Patent Application No. 62/452,398 filed Jan. 31, 2017, the entire disclosure of which is incorporated by reference herein.

TECHNICAL FIELD

The present disclosure relates to surgical devices and/or systems for performing endoscopic surgical procedures. More specifically, the present disclosure relates to surgical devices and/or systems for applying fasteners such as tacks to target tissue sites in a patient. The present disclosure also relates to methods of use and/or manufacture of such surgical devices and/or systems.

BACKGROUND

During laparoscopic or endoscopic surgical procedures, access to a surgical site is often achieved through an end effector of a narrow instrument shaft of an endoscopic surgical device inserted through a small entrance wound or incision in a patient. Given the solemnity of these types of surgical procedures, it is imperative that such endoscopic surgical devices maintain their functional and structural integrity throughout these surgical procedures.

Many instrument shafts of these endoscopic surgical devices support fasteners, such as tacks, that may be dispensed from the end effectors of the instrument shafts into a target tissue site, for example, to secure a mesh to the target tissue site.

Such endoscopic surgical devices typically include a handle from which the instrument shaft extends. The handle imparts rotation on the tacks for advancing the tacks through the instrument shaft and/or end effector.

To effectuate the rotation of the tacks through the instrument shaft and/or end effector, a spring can be affixed (by laser welding, for example) to an inside diameter of the instrument shaft and/or end effector. While easy to use, fabrication of such instrument shafts and/or end effectors require extensive effort including manufacturing the tubing, cutting the tubing to length, forming a spring, loading the spring on a mandrel, and affixing the spring (by laser welding, for example) at predetermined intervals along the drawn and cut tubing. After fabrication of the instrument shaft, the mandrel can then be removed so that the instrument shaft can be directly or indirectly coupled to the handle.

During use, a clinician may need to torque, twist, axially load or otherwise manipulate the end effector in vivo in order to reach and perform intended function in certain remote target areas. Such manipulation of the end effector requires the end effector to maintain a certain structural stiffness to resist undesirable bending so that there is no disruption in tack delivery. More specifically, such manipulation of the end effector requires the end effector to maintain sufficient torsional and cantilever load rigidity in order to minimize disruption in tack delivery.

Accordingly, a need exists for endoscopic surgical devices that maintain functional and structural integrity for dispensing fasteners during surgical procedures, that are easy to use, and that are economical to manufacture.

SUMMARY

The embodiments of the endoscopic surgical devices or end effectors of the present disclosure advantageously lower manufacturing costs and effort while optimizing the structure that provides functional improvements to tack guidance, tack deployment, stiffness, loadability, and resilience. For example, the need to weld or otherwise affix additional structures into an outer tube of the end effector, which additional structures help to guide the advancement and firing of tacks from the end effector, is eliminated.

The present endoscopic surgical devices or end effectors thereof include outer tubes defining fastener guidance features formed therein. The outer tubes include inner ridges, or depressions) or depressions that extend into a central lumen of the outer tube. One or more of these inner ridges or depressions may include a helical arrangement to guide the fasteners through the outer tube as these fasteners are rotated relative to the outer tube by an inner tube. In order to limit flexing or deflection of the outer tubes, in embodiments, the outer tubes may include one or more longitudinally extending ribs that increase stiffness or rigidity of the outer tube.

According to one aspect of the present disclosure, a surgical fastening device includes a handle, a shaft extending from the handle, and an end effector supported on the shaft. The end effector supports one or more fasteners and includes a tube defining a longitudinal axis. The tube includes an outer surface and an inner surface. The inner surface of the tube defines a lumen that extends along the longitudinal axis of the tube. The tube defines depressions that may be arranged helically about the inner surface of the tube along the longitudinal axis to guide fasteners through the lumen. The end effector may further include one or more ribs extending along the tube. The depressions and/or the ribs may extend a full length of the tube, or may extend along any portion of the full length of the tube.

In some embodiments, the depressions are defined by recesses in the outer surface of the tube. The depressions form grooves at predetermined locations along the tube. The grooves may be disposed between inner ridges configured to contact the fasteners as the fasteners advance through the lumen.

In certain embodiments, the surgical fastening device may further include a drive member supported within the tube. The drive member may be rotatable relative to the tube to distally advance fasteners along the tube.

In some embodiments, one or more ribs interrupt adjacent depressions along the tube. The ribs may be positioned at predetermined radial locations about the tube to increase stiffness of the tube. In embodiment, there may be three such ribs.

In certain embodiments, the depressions in the tube may be roll formed in the tube. In some embodiments, the depressions may be stamped/cold formed in the tube. In additional embodiment, the depressions may be formed by a rolling process and/or an electroforming process.

According to another aspect of the present disclosure, an end effector includes one or more fasteners, a tube defining a longitudinal axis, and one or more ribs. The tube includes an outer surface and an inner surface. The inner surface defines a lumen that extends along the longitudinal axis. The tube includes inner ridges to guide the fasteners through the lumen. The inner ridges may be disposed in a helical arrangement along the longitudinal axis and may have an interrupted pattern. The end effector may include one or more ribs extending along the tube. The ridges and/or the ribs may extend a full length of the tube, or may extend along any portion of the full length of the tube.

In some embodiments, the inner ridges are formed by depressions defined in the outer surface of the tube.

In certain embodiments, the end effector may further include a drive member supported within the tube.

In some embodiments, one or more ribs extend longitudinally along the outer surface of the tube. The ribs may create the interrupted pattern by interrupting adjacent ridges. In embodiments, the ribs may be supported at spaced apart locations around the tube.

In certain embodiments, the inner ridges may be stamped/formed in the tube. In some embodiments, the inner ridges may be formed by piercing and folding the features into the tube.

According to yet another aspect of the present disclosure, an end effector for a surgical fastening device includes a fastener and a tube defining a longitudinal axis. The tube includes an outer surface and an inner surface. The inner surface of the tube defines a lumen that extends along the longitudinal axis of the tube. The inner surface of the tube defines depressions that are arranged about the tube along the longitudinal axis. One or more of the depressions may be configured to prevent proximal movement of the fastener through the lumen and one or more of the depressions may be configured to facilitate distal advancement of the fastener through the lumen.

In some embodiments, the depressions may form inner grooves at predetermined locations along the inner surface of the tube.

In certain embodiments, the tube may include one or more ribs that extend longitudinally along the tube.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 6D is a cross-sectional view of the outer tube of FIGS. 6A and 6B, as taken along line 6D-6D shown in FIG. 6A;

FIG. 6E is a proximal end view of the outer tube of FIGS. 6A and 6B;

FIG. 6F is a distal end view of the outer tube of FIGS. 6A and 6B;

FIG. 6G is an enlarged, perspective view of the indicated area of detail shown in FIG. 6A;

DETAILED DESCRIPTION

Figure 1:
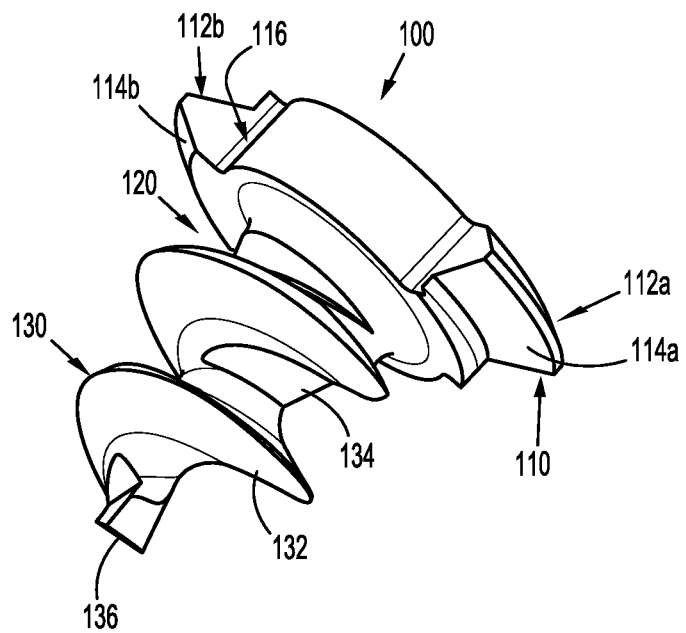
FIG. 1 is a perspective view of a surgical fastener for use in an endoscopic surgical device in accordance with the present disclosure.
Figure 2:
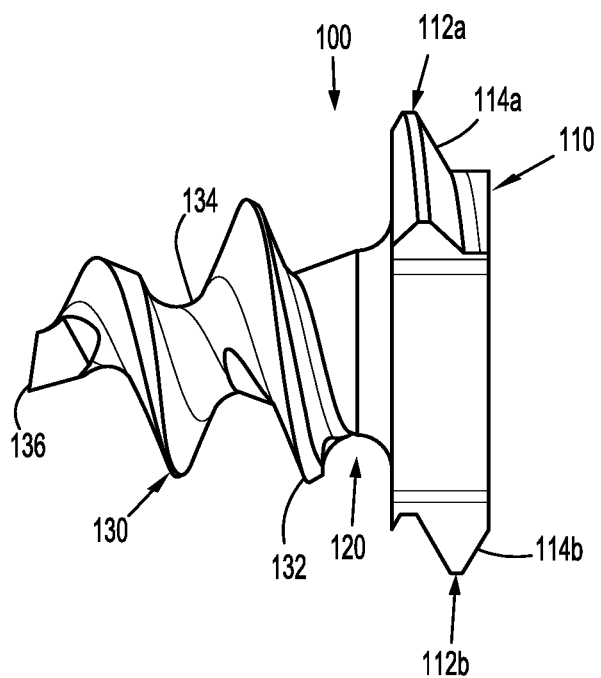
FIG. 2 is a side, elevational view of the surgical fastener of FIG. 1.
Figure 3:
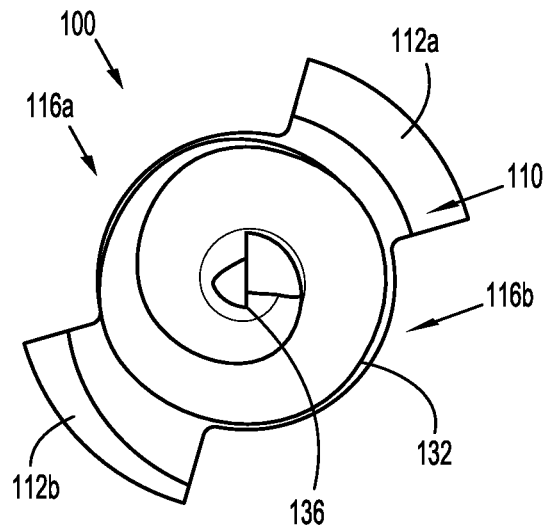
FIG. 3 is a distal, end view of the surgical fastener of FIGS. 1 and 2.

Embodiments of endoscopic surgical devices and end effectors in accordance with the present disclosure are described in detail with reference to the drawings, in which like reference numerals designate identical or corresponding elements in each of the several views. As used herein, the term "distal" refers to that portion of the device that is farther from the user, while the term "proximal" refers to that portion of the device that is closer to the user. As commonly known, the term "clinician" refers to a doctor, a nurse or any other care provider, and may include support personnel. In the following description, well-known functions or constructions are not described in detail to avoid obscuring the present disclosure in unnecessary detail.

Non-limiting examples of endoscopic surgical devices according to the present disclosure include manual, mechanical and/or electromechanical surgical tack appliers (e.g., tackers) and the like.

Referring initially to FIGS. 1-4, an illustrative embodiment of a surgical fastener or tack for use with the endoscopic surgical devices of the present disclosure is illustrated and generally designated as an anchor 100. As seen in FIGS. 1-4, the anchor 100 includes a head section 110, a mesh retention section 120, and a threaded tissue-snaring section 130. The head section 110 of the anchor 100 includes a pair of opposing threaded sections 112a, 112b having respective radially, outer, helical head threads 114a, 114b, and a pair of opposing open or slotted sections 116a, 116b. A distal surface of the head section 110 is formed onto or integral with a proximal end of the mesh retention section 120.

The mesh retention section 120 of the anchor 100 extends from and between a distal end or surface of the head section 110 of the anchor 100 and a proximal end of the tissue-snaring section 130 of the anchor 100. The mesh retention section 120 functions to lock, anchor or otherwise retain a surgical mesh "M" (FIG. 9) onto the anchor 100 when the anchor 100 is screwed into the surgical mesh "M" to a depth past a proximal-most segment 138 of the tissue-snaring thread 132 of the tissue-snaring section 130. This is achieved because there is no thread located in the mesh retention section 120 that would enable the anchor 100 to be unscrewed or backed out from the surgical mesh "M".

The mesh retention section 120 of the anchor 100 has a cylindrical or conical transverse cross-sectional profile. The mesh retention section 120 includes a transverse radial dimension, relative to a central longitudinal axis of the anchor 100, that is smaller than a transverse radial dimension of the head section 110 of the anchor 100, and smaller than a transverse radial dimension of the proximal-most segment 138 of the tissue-snaring thread 138 of the anchor 100.

The threaded tissue-snaring section 130 of the anchor 100 includes helical threads 132 formed onto a tapered truncated body section 134. A distal point or tip 136 of the anchor 100 defines the terminus of the distal most tissue-snaring thread 132.

Figure 4:
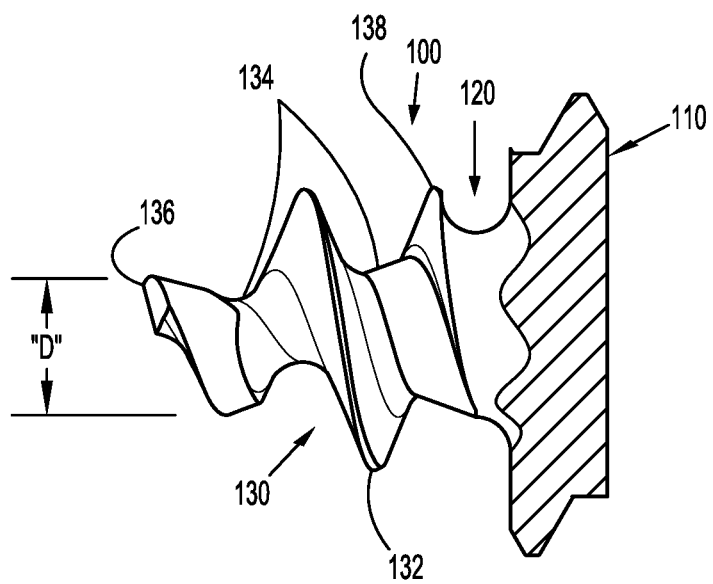
FIG. 4 is a side, elevational view, partially broken away, of the surgical fastener of FIGS. 1-3.

As seen in FIG. 4, the body section 134 of the tissue-snaring section 130 is tapered, e.g., becoming smaller toward the distal end of the threaded tissue-snaring section 130. The body section 134 includes a concave taper. The tissue-snaring threads 132 of the anchor 100 terminate at the distal tip 136 of the anchor 100.

The anchor 100 may be constructed from any suitable bioabsorbable material, such as, for example polylactide, polyglycolide, polylactide-co-glycolide or the like. In some embodiments, the anchor may be formed of a co-polymer. The anchor 100 may be formed of a solid, non-cannulated configuration.

Figure 5:
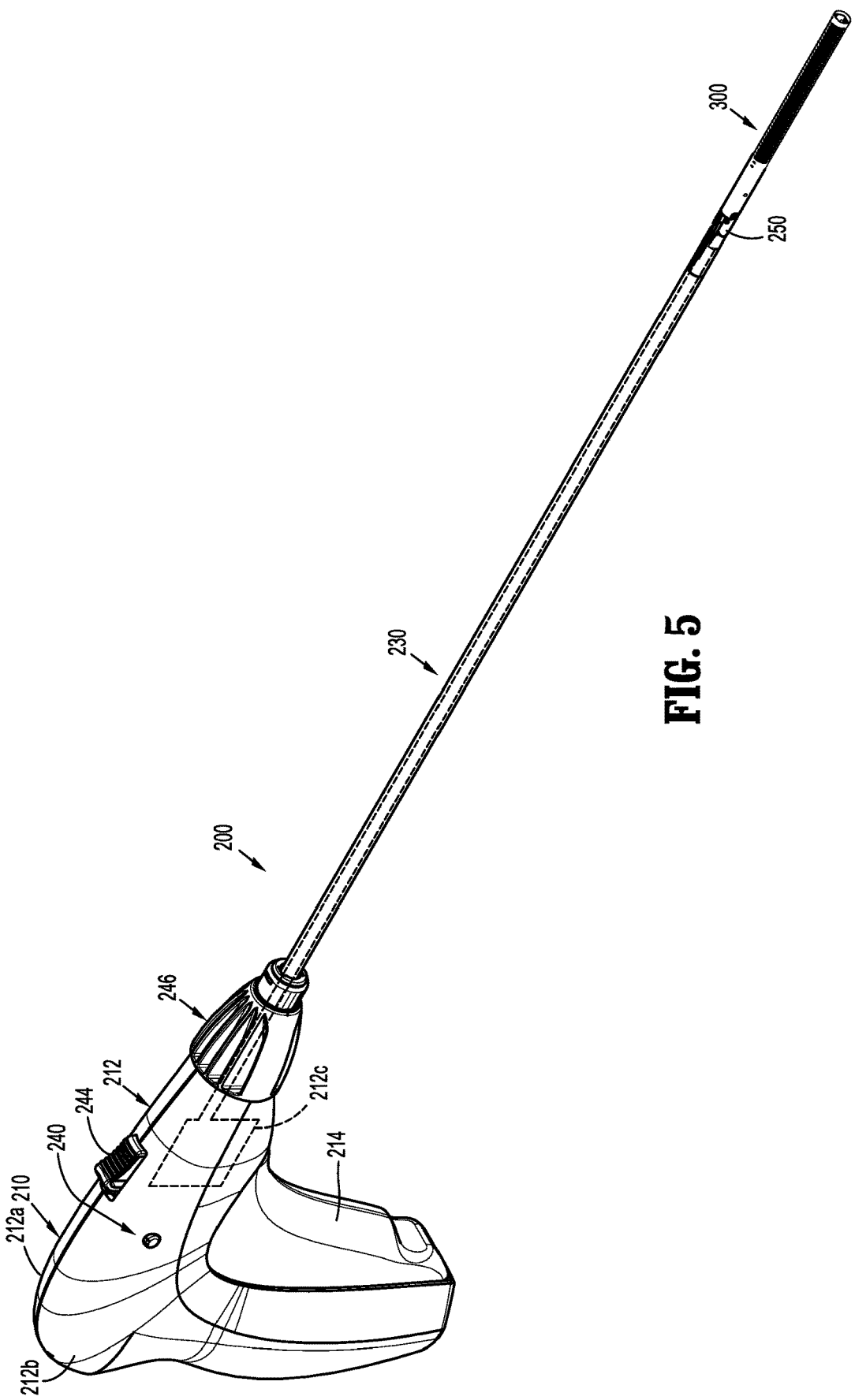
FIG. 5 is a perspective view of an endoscopic surgical device having one embodiment of an end effector supported thereon in accordance with the present disclosure.

Turning now to FIG. 5, an endoscopic surgical device, in the form of an endoscopic surgical tack applier or tacker, is shown generally as 200. The tack applier 200 includes a handle assembly 210 and an endoscopic assembly 230 extending from the handle assembly 210 to an end effector 300. The tack applier 200 may be a reusable device which may be cleaned, sterilized and/or autoclaved for reuse following a surgical procedure, and which may be used with a plurality of end effectors 300 during a single surgical procedure. The end effector 300 of the endoscopic assembly 230 is a reload and may be in the form of a single use loading unit (SULU) or disposable loading unit (DLU). The tack applier 200 is configured to store and selectively dispense or fire the anchors 100 from the end effector 300 and into the surgical mesh "M" overlying tissue.

As seen in FIG. 5, the handle assembly 210 of the tack applier 200 includes a handle housing 212 formed from a first half-section 212a and a second half section 212b joined to one another. The first half-section 212a and the second half section 212b of the handle housing 212 may be joined to one another using methods known by those with skill in the art, including and not limited to welding, mechanical press fit, fastening (e.g., with screws), and the like.

The handle assembly 210 of the tack applier 200 includes a trigger 214 pivotably connected to the handle housing 212 at a location remote from the endoscopic assembly 230. The trigger 214 is movable from an extended or un-actuated position to a retracted or actuated position to fire the anchors 100 from the end effector 300. The trigger 214 may be spring-biased towards to the un-actuated position and operably coupled to a drive assembly 212c supported in the handle assembly 210 and the endoscopic assembly 230.

The handle assembly 210 of the tack applier 200 includes a button 240 and a slider 244 supported on the handle housing 212. The slider 244 is configured to effectuate a loading/retention and/or a release/removal of the end effector 300 to/from the endoscopic assembly 230. The button 240 is configured to selectively enable and/or inhibit actuation of the trigger 214 of the handle assembly 210, so that a clinician can, for example, safely effectuate a loading/retention, and/or a release/removal, of an end effector 300 to/from the endoscopic assembly 230 of the tack applier 200.

The handle assembly 210 further includes an articulation knob 246 rotatably supported on handle housing 212 and operably coupled to the anchor retaining/advancing assembly 230. Rotation of articulation knob 246 results in the articulating and/or straightening of the end effector 300 about an articulation joint 250 relative to the anchor retaining/advancing assembly 230.

For a detailed description of the construction and operation of a similar endoscopic surgical devices having one or more of the same or similar components for use with one or more components of the presently described endoscopic surgical devices, reference may be made to U.S. Patent Application Publication No. 2015/0005748, the entire contents of which are incorporated by reference herein.

Figure 6A:
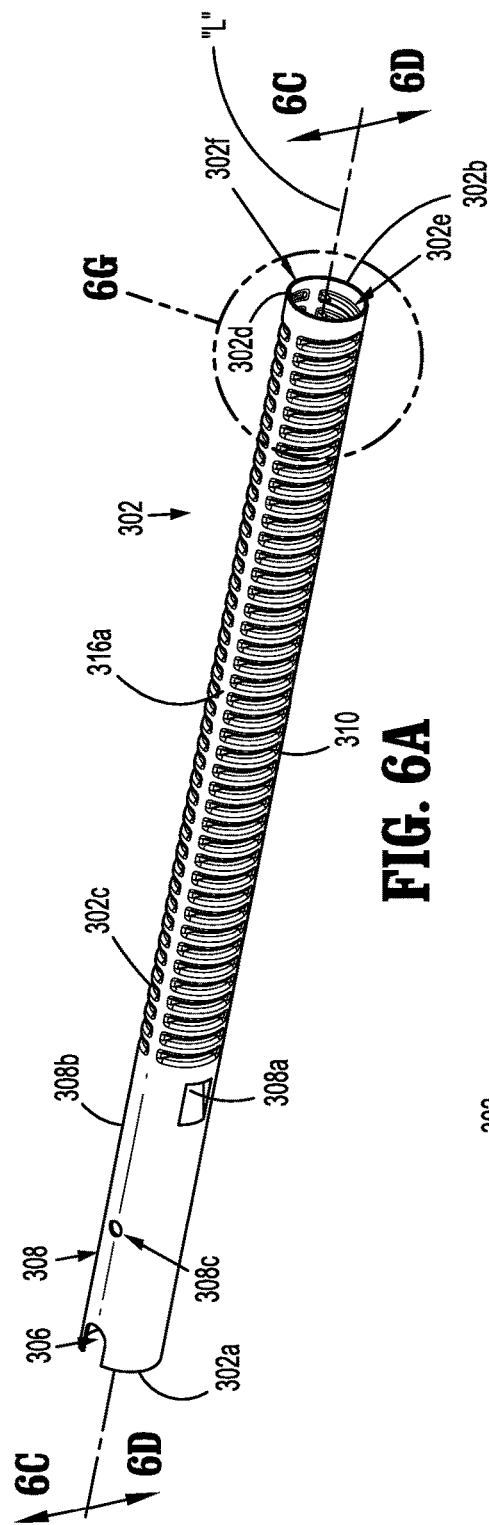
FIG. 6A is an enlarged, perspective view of an outer tube of the end effector shown in FIG. 5.
Figure 6B:
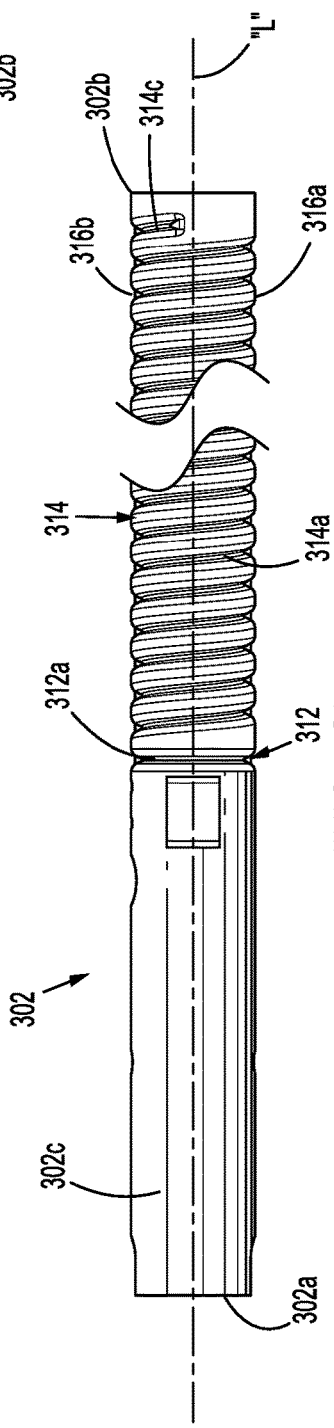
FIG. 6B is a top view of the outer tube of FIG. 6A.
Figure 6C:
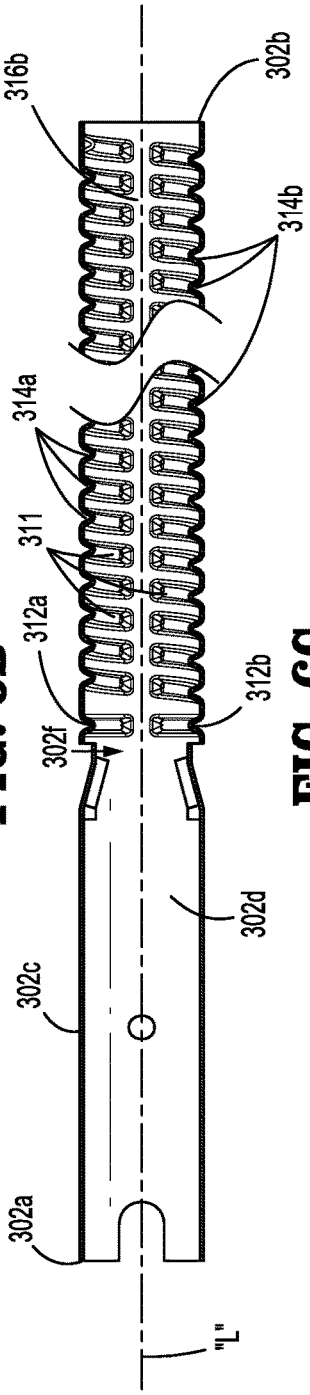
FIG. 6C is a cross-sectional view of the outer tube of FIGS. 6A and 6B, as taken along line 6C-6C shown in FIG. 6A.
Figure 7:
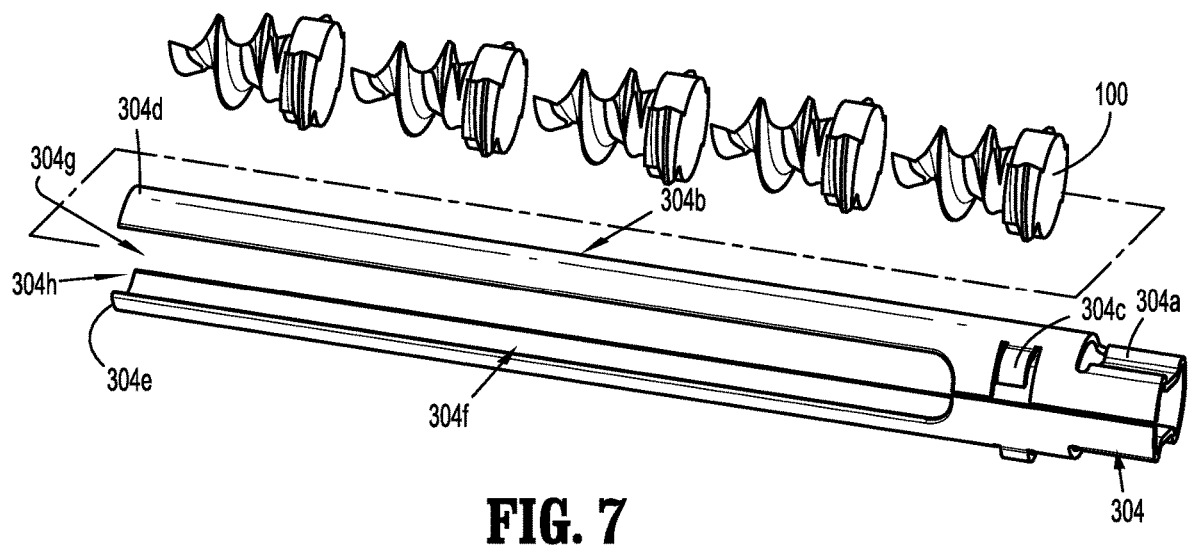
FIG. 7 is a perspective view of an inner tube of the end effector of FIG. 5 with a plurality of surgical fasteners of FIGS. 1-4 shown separated therefrom.

Turning now to FIGS. 5-7, the end effector 300 is selectively connectable to a distal portion of the endoscopic assembly 230 and may be in the form of a reload. In some embodiments, end effector 300 may be disposable, autoclavable/sterilizable and/or reusable. The end effector 300 includes an outer tube 302 and an inner tube 304 rotatably supported within the outer tube 302. The inner tube 304 supports the surgical anchors 100 therein and is rotatable relative to the outer tube 302 to axially advance the surgical anchors 100 through the outer tube 302.

With reference to FIG. 6A, the outer tube 302 of the end effector 300 defines a longitudinal axis "L" that extends between a proximal end portion 302a of the outer tube 302 and a distal end portion 302b of the outer tube 302. The proximal end portion 302a defines a key slot 306 for engagement with a complementary key (not shown) formed on a distal end portion of the endoscopic assembly 230 to align the end effector 300 and the endoscopic assembly 230 with one another. The outer tube 302 further includes an outer surface 302c and an inner surface 302d. The inner surface 302d of the outer tube 302 defines a lumen 302e that extends through the outer tube 302 along the longitudinal axis "L." The outer tube 302 further includes a proximal portion 308 and a distal portion 310 that extends distally from the proximal portion 308. The proximal portion 308 extends distally to features (e.g., tabs) 308a, 308b that project inwardly toward the lumen 302e and prevents the inner tube 304 from translating proximally. The proximal portion 308 may further define a wedge opening 308c transversely therethrough to support a shipping wedge (see FIG. 10). The distal portion 210 extends distally from the proximal portion 308 to a distal end opening 302f of the outer tube 302 that is in registration with the lumen 302e of the outer tube 302.

Referring to FIGS. 6B-6G, the distal portion 310 of the outer tube 302 includes a proximal depression 312 that may extend circumferentially about the outer tube 302 at a single longitudinal location along the longitudinal axis "L." The proximal depression 312 functions as a constraining feature or constraining diameter to limit distal movement of the inner tube 304 relative to the outer tube 302. The distal portion 310 further includes distal depressions 314 arranged along the longitudinal axis "L" and spaced apart from the proximal depression 312. The distal depressions 314 may be helically arranged about the outer tube 302. Each of the distal depressions 314 may have an identical arc length as one or more of the other distal depressions 314. The proximal and distal depressions 312, 314 may be depressed (e.g., rolled, stamped, crimped, deposited on a mandrel or plate, or otherwise formed etc.) into the outer surface 302c such that the proximal and distal depressions 312, 314 are recessed into the outer surface 302c and project radially inwardly from the inner surface 302d to form a plurality of inner ridges 313 extending into the lumen 302e of the outer tube 302. The inner ridges 313 may be a trough of the respective depressions 312, 314.

Disposed adjacent to the depressions 312, 314, on the outer surface 302c of the outer tube 302, are outer ridges 315 that may be formed by virtue of the formation of the depressions 312, 314. The inner ridges 313 define a plurality of inner grooves 311 on the inner surface 302d of the outer tube 302, which are positioned to enable the anchors 100 to be axially advanced through the outer tube 302 upon rotation of the anchors 100 through the inner grooves 311.

The proximal and distal depressions 312, 314 of the distal portion 310 of the outer tube 302 are separated (e.g., interrupted) by one or more stiffness members or ribs 316a, 316b that extend longitudinally along the distal portion 310 of the outer tube 302 and function to increase the structural stiffness and limit deflection of the outer tube 302. The ribs 316a, 316b (and so on, depending on the number of ribs) separate the proximal depression 312 into segments (depicted as a first segment 312a and a second segment 312b for a two-rib design), and the distal depressions 314 into segments (depicted as a first and second segments 314a, 314b for a two-rib design) such that each depression 312, 314 has an interrupted profile. With this interrupted profile, each of the depressions 312, 314 is discontinuous, with ends of continuous segments of respective depressions 312, 314 spaced apart along an arc length corresponding to a width of the respective ribs 316a, 316b (and so on, depending on the number of ribs). This interrupted profile may provide each depression of the proximal and distal depressions 312, 314 with a first end 318a and a second end 318b, as seen in FIGS. 6E and 6F. With the ribs 316a, 316b (and so on, depending on the number of ribs) separating each of the depressions 312, 314, each of the depressions 312, 314 has an arc length less than 360 degrees.

The distal depressions 314 of the distal portion 310 further include a distal-most segment 314c that may circumscribe a different arc length about the circumference of the outer tube 302 (e.g., circumscribes a shorter or longer arc length about the circumference of the outer tube 302) than the arc lengths of one or more of the other segments 314a, 314b (and so on, depending on the number of ribs) of the distal depressions 314 to effectuate proper release of the anchors 100 through the distal end opening 302f of the outer tube 302 as the anchors 100 are dispensed out of the outer tube 302.

With reference to FIG. 7, the inner tube 304 of the end effector 300 is rotatably disposed within the outer tube 302 of the end effector 300. The inner tube 304 includes a proximal end portion 304a and a distal end portion 304b. The proximal end portion 304a is configured to couple to the drive assembly 212c of the tack applier 200 (FIG. 5). The inner tube 304 includes retention tabs 304c projecting radially outward therefrom. In some embodiments, the inner tube 304 includes three retention tabs 304c disposed about a circumference at offset locations about the circumference. The retention tabs 304c are axially fixed and rotatably seated in a slot 302f (FIG. 6C) defined by the outer tube 302 between a proximal surface of the depression 312 of the outer tube 302 and a distal surface of the features (e.g., tabs) 308a, 308b of the outer tube 302. In some embodiments, the retention tabs 304c may be in the form of one or more annular rings circumscribing the inner tube 304.

When the inner and outer tubes 304, 302 are assembled together, the inner tube 304 may be advanced through the proximal end of the outer tube 302 such that the tabs 308a, 308b of the outer tube 302 are deflected radially outwardly from an initial position by the insertion of the inner tube 304 into the outer tube 302 until after the retention tabs 304c are advanced distally past the tabs 308a, 308b of the outer tube 302. After the retention tabs 304c of the inner tube 304 are advanced distally past the tabs 308a, 308b of the outer tube 302, the tabs 308a, 308b of the outer tube 302, which may be formed of resilient material, deflect or bias radially inwardly back to their initial position. With the inner and outer tubes 304, 302 assembled together, the tabs 308a, 308b of the outer tube 302 prevent the inner tube 304 from moving proximally relative to the outer tube 302 and the proximal surface of the depression 312 prevents the inner tube 304 from moving distally relative to the outer tube 302 such that the inner tube 304 is axially fixed relative to the outer tube 302. While the inner tube 304 is axially fixed relative to the outer tube 302, the inner tube 304 can rotate relative to the outer tube 302 with the retention tabs 302c rotatable through the slot 302f of the outer tube 302.

The distal end portion 304b of the inner tube 304 defines a pair of tines 304d, 304e separated by channels 304f, 304g that extend into a central lumen 304h of the inner tube 304. The distal end portion 304b of the inner tube 304 is configured to receive and support a plurality of anchors 100 within the central lumen 304h of the inner tube 304. In particular, the anchors 100 are loaded into the end effector 300 such that the pair of opposing threaded sections 112a, 112b of the anchors 100 extend through the respective channels 304f, 304g of the distal end portion 304b of the inner tube 304 and are rotatably disposed within the inner grooves 311 of the outer tube 311. The pair of tines 304d, 304e of the distal end portion 304b of the inner tube 304 are disposed within the pair of slotted sections 116a, 116b of the anchors 100 to rotatably drive the anchors 100 through the inner grooves 311 of the outer tube 302 and axially along the longitudinal axis "L" and the central lumen 304h of the inner tube 304. Each anchor 100 is loaded into the end effector 300 such that adjacent anchors 100 are not in contact with one another so as to not damage the distal tips 136 of the anchors 100.

Figure 8A:
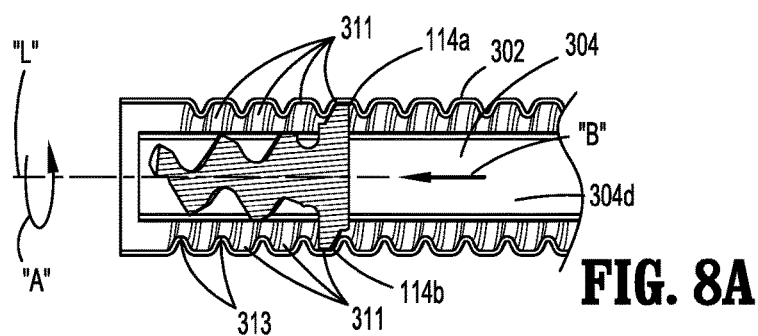
FIG. 8A-8C are progressive, cross-sectional views of a distal portion of the end effector of FIG. 5, illustrating the surgical fasteners of FIGS. 1-4 being advanced therethrough.
Figure 8B:
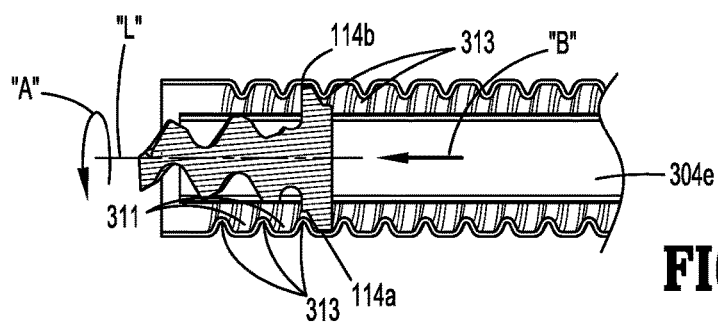
Figure 8C:
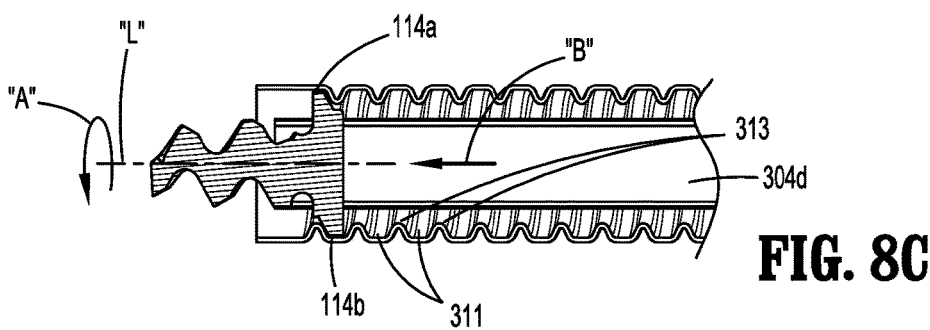

In use, actuation of the trigger 214 of the tack applier 200 causes the drive assembly 212c to transmit rotation to the inner tube 304 of the end effector 300. As inner tube 304 is rotated, as indicated by arrows "A," about longitudinal axis "L" (see FIGS. 8A-8C), and with respect to the inner grooves 311 of the outer tube 302, the tines 304d, 304e of inner tube 304 transmit the rotation to the anchors 100 (only one anchor 100 shown) and advance the anchors 100 distally, as indicated by arrows "B," owing to the head threads 114a, 114b of the anchors 100 engaging with the inner grooves 311 and inner ridges 313 of the outer tube 302. Although only a single anchor 100 is shown in FIGS. 8A-8C for illustrative purposes, the inner tube 304 can transmit rotation to an entire stack of anchors 100 and simultaneously advance the entire stack of anchors 100 distally in response to rotation of the inner tube 304 relative to the outer tube 302 as described above.

One or more components of the tack applier 200 and anchors 100 may be configured such that a single complete and full actuation of the trigger 214 may result in a firing of a single anchor 100 (e.g., the distal-most anchor of the stack of anchors 100 loaded in end effector 300) from the end effector 300.

Figure 9:
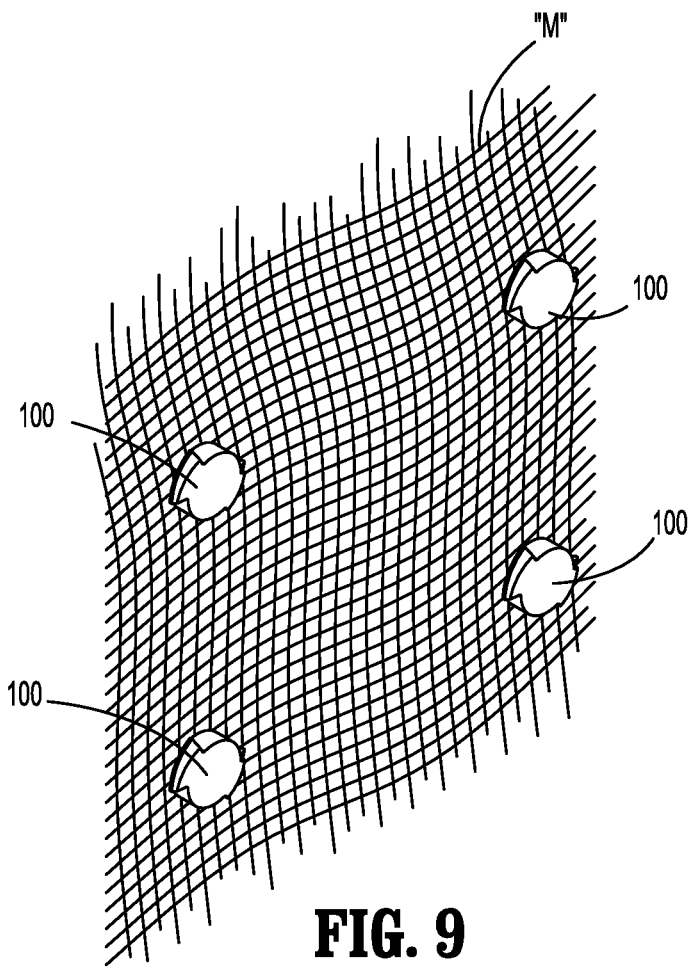
FIG. 9 is a perspective illustration showing the anchoring and/or fixation of a surgical mesh to underlying tissue with a plurality of surgical fasteners of the endoscopic surgical device of FIG. 5.

The tack applier 200 may be repeatedly fired to fire the anchors 100 from the end effector 300, for example, into the surgical mesh "M" as seen in FIG. 9, until the surgical procedure is complete or until the end effector 300 is spent of the anchors 100. If end effector 300 is spent of the anchors 100, and if additional anchors 100 are required to complete the surgical procedure, the spent end effector 300 may be replaced with a new (e.g., loaded with anchors 100) end effector 300.

Figure 10:
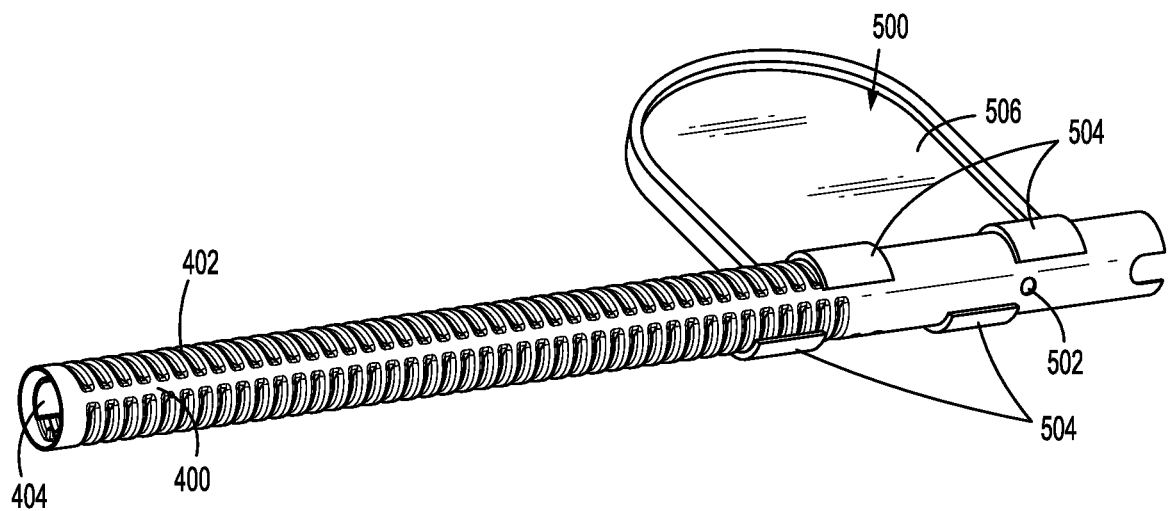
FIG. 10 is a perspective view of another embodiment of an end effector of the endoscopic surgical device of FIG. 5, the end effector having a shipping wedge secured thereto.
Figure 11A:
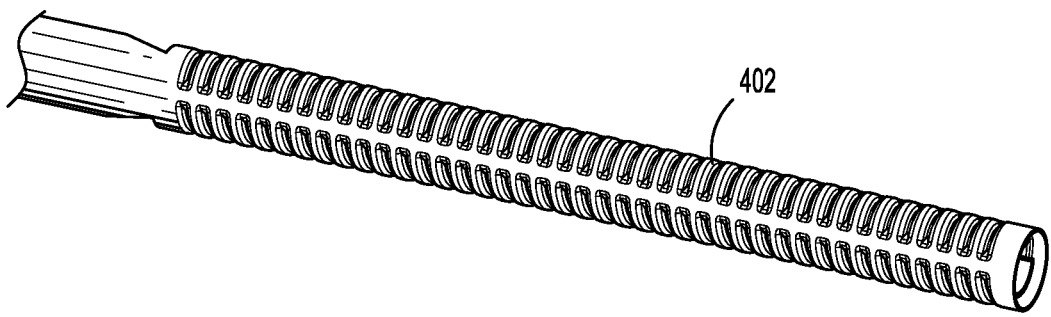
FIG. 11A is a perspective view of the end effector of FIG. 10.
Figure 11B:
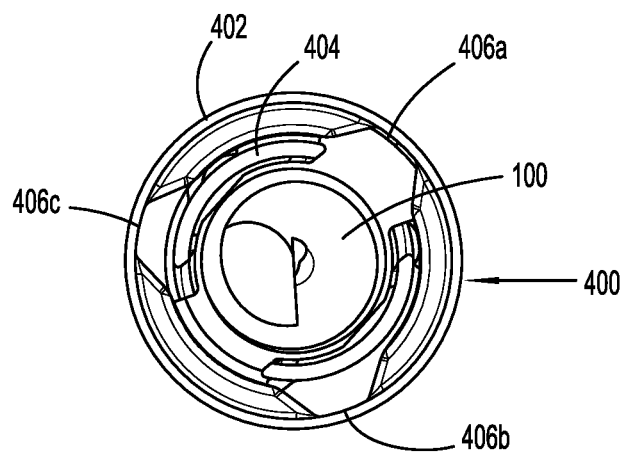
FIG. 11B is a distal end view of the end effector of FIG. 11A.

Turning now to FIGS. 10, 11A, and 11B, another embodiment of an end effector, generally referred to as end effector 400, is substantially similar to end effector 300 and therefore is only described herein to the extent necessary to explain the differences in construction and operation of the end effector 400. The end effector 400 includes an outer tube 402 and an inner tube 404 that releasably support one or more anchors 100.

The outer tube 402 includes three spaced-apart ribs 406a, 406b, and 406c to increase rigidity/stiffness. Such increased rigidity and/or structural stiffness may be provided in multiple planes, directions, and/or angles. By comparison, the outer tube 302 of the end effector 300 only has two ribs 316a, 316b, which provides relatively less stiffness than embodiments with more ribs, but also provides greater flexibility than embodiments with more ribs, such as the outer tube 402 of the end effector 400. Accordingly, although the outer tube 402 has relatively more stiffness, and therefore relatively greater rigidity than the outer tube 302 of the end effector 300, the outer tube 302 of the end effector 300 has relatively greater contact with the anchors 100 (e.g., each rib interrupts the inner groove/ridge profile of the respective embodiment of the outer tube), and therefore, depending on relative geometries, has relatively increased fastener guidance through the end effector 300.

In embodiments, the ribs of the present disclosure may be positioned at relatively spaced-apart locations about the circumference of the presently disclosed outer tubes such that the pair of opposing threaded sections 112a, 112b of the anchor 100 do not simultaneously engage (in some embodiments fully engaged, in other embodiments, partially engaged) two diametrically opposed ribs (e.g., ribs exactly 180 degrees apart and/or ribs approximately 180 degrees apart) as the anchor 100 rotates through the outer tube. Advantageously, such positioning of the ribs prevents the anchor 100 from misfiring and/or misaligning as the anchor 100 rotates relative to the outer tube. For example, in an embodiment with three ribs, the three ribs can be annularly spaced apart such that no two of the three ribs are diametrically opposed, whereby only one of the thread sections 112a, 112b of the anchor 100 is engaged with the ribs (e.g., one of the three ribs) at a time. In embodiments with more ribs, for instance five or more ribs, both threaded sections 112a, 112b of the anchor 100 may be at least partially engaged with two different ribs, but such ribs will not be diametrically opposed, thereby preventing misfire and/or misalignment of an anchor 100.

As seen in FIG. 10, a shipping wedge 500 may be provided with any of the disclosed embodiments of end effectors. The shipping wedge 500 is configured to releasably connect to one of the presently disclosed end effectors. For example, the shipping wedge 500 may include a pin 502 that extends through the end effector 400 and wings 504 that capture the end effector 400 to secure the shipping wedge 500 to the end effector 400. While the shipping wedge 500 is coupled to the end effector 400, the pin 502 of the shipping wedge 500 inhibits premature rotation of the inner tube 404 of the end effector 400 and helps to facilitate loading/unloading of the end effector 400 to/from the tack applier 200. The shipping wedge 500 further includes a handle portion 506 to facilitate gripping thereof.

Figure 12A:
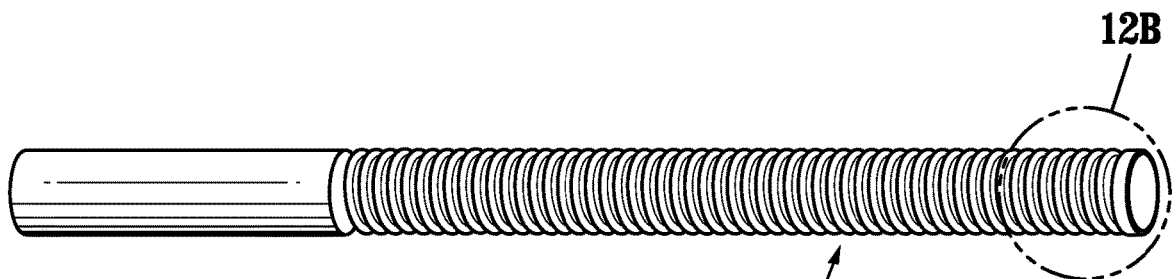
FIG. 12A is a perspective view of an outer tube of another embodiment of an end effector of the endoscopic surgical device of FIG. 5.
Figure 12B:
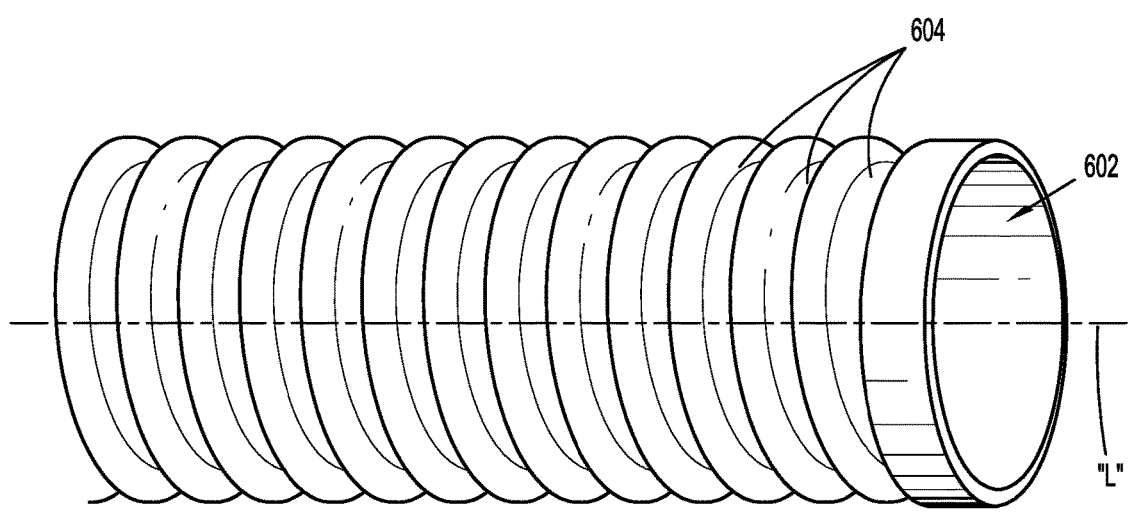
FIG. 12B is an enlarged, perspective view of the indicated area of detail shown in FIG. 12A.
Figure 12C:
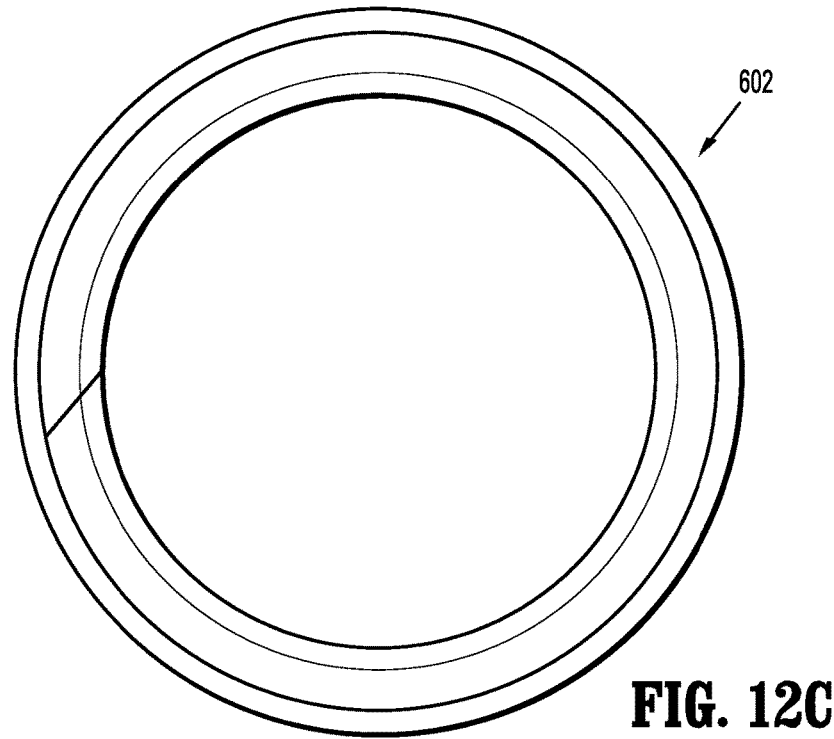
FIG. 12C is a distal end view of the outer tube of FIG. 12A.

Turning now to FIGS. 12A-12C, yet another embodiment of an outer tube, generally referred to as outer tube 602, is substantially similar to outer tubes 302, 402 and therefore is only described herein to the extent necessary to explain the differences in construction and operation of the outer tube 602. While the outer tube 602 is similar to outer tubes 302, 402, the outer tube 602 does not include any ribs to increase flexibility/deflectability of the outer tube 602 so that respective depressions, grooves, and inner/outer ridges thereof may have continuous or substantially continuous arrangements about the outer tube 602. For example, depressions 604 of the outer tube 602 may have a single continuous helical arrangement about the outer tube 602 along the longitudinal axis "L" thereof.

In certain embodiments of the outer tube, instead of forming inner ridges by depression, the outer tube may include inner ridges that are in the form of threads and may be, formed by cutting away material, not displacing material by depression.

In some embodiments of the outer tube, one or more of the presently disclosed ribs may be discontinuous along one or more portions of a length of the respective ribs, whereby such ribs define a plurality of spaced-apart longitudinal segments. Such ribs may define one or more depressions having one or more varying arc lengths along the length of the longitudinal axis "X." In some embodiments of the outer tube, one or more of the depressions of the outer tube may cross over one or more ribs of the outer tube.

In certain embodiments, one or more of the depressions can be formed in the outer tube with one or more stamping forming dies (not shown) that are configured to form the one or more ribs. The depressions or ridges may also be formed by rolling, piercing and forming, cold forming, etc. The depression forming tooling may include both inner and outer contact/forming tools. The outer forming tools may include one or more stamping/forming dies, and will define the depression and/or rib geometry imparted to outer surface 402 of outer tube 402. The inner forming tool may be an arbor that will define the geometry imparted to an inner surface of outer tube 402. In general, the arbor geometry will closely resemble the negative of the outer forming die geometry. Depending on configuration, the arbor tool may be removed from finished part by rotation (unscrewed) or by use of collapsible tool technology.

In embodiments, the ribs do not interrupt the inner surface of the presently disclosed outer tube. In some embodiments, the ribs extend only along the outer surface of the presently disclosed outer tube. In certain embodiments, to further increase guidance of tissue along the ribs or insertion of the outer tube into tissue, a secondary set of inner ridges may be formed on the inner surface of the presently disclosed outer tube along the ribs thereof so as to align (e.g., helically) with a primary set of inner ridges as defined by the depressions of the presently disclosed outer tube detailed above.

Although some of the embodiments of the outer tube are shown with two or three ribs, the presently disclosed outer tubes can include any number of ribs (e.g., 0, 1, 2, 3, 4, 5, 6 . . . n). Such ribs may be spaced apart at any suitable annular angle between 0 and 360 degrees relative to one another. For instance, in some embodiments, adjacent ribs may be annularly spaced apart less or equal to than about 180 degrees relative to one another, while in certain embodiments, adjacent ribs may be annularly spaced apart less than or equal to about 90 degrees relative to one another. In an embodiment, adjacent ribs may be annularly spaced apart by about 120 degrees relative to one another. The presently disclosed ribs can be provided in any suitable configuration such as splines, coils, tabs, shafts, rods, tubes, cables, wires, etc. and/or combinations thereof. In certain embodiments, one or more the ribs may include nonlinear (e.g., curved and/or arcuate, such as c and/or s-shaped) and/or linear profiles.

The presently disclosed outer tubes, or portions thereof (e.g., one or more of the ribs), may have any suitable dimension. For example, embodiments of the outer tube may have a length between about 2 inches and about 4 inches, and/or a thickness that ranges between about 0.005 inches and about 0.02 inches, particularly between about 0.009 inches and about 0.015 inches, and more particularly between about 0.011 and about 0.013 inches. In some embodiments, the presently disclosed outer tubes, or portions thereof, may have variable thicknesses along the length thereof that are configured to optimize deflection and/or structural stiffness properties. For instance, the proximal end portion of the outer tube, or portions thereof, may include a first thickness that is different from a distal end portion of the outer tube, or portions thereof. Or, in certain embodiments, the thickness of the outer tube may have a predetermined gradient, or multiple gradients, along a length, or portions of the length thereof.

The presently disclosed outer tubes, or portions thereof, can be formed of, or provided with, any suitable material. In some embodiments, the presently disclosed outer tubes, or portions thereof, may be formed of different materials. Suitable materials include, and are not limited to, stainless steel, titanium, and nickel-titanium (also known as Nitinol) for shape-memory properties.

With reference to Table 1 below, the following data was compiled using finite element analysis to compare tip deflection of different outer tube designs under identical bending load applied to distal end.

TABLE 1

| Tubes | Distal Tip Deflection of a Simplified 1" Unit Length Tube (in) | Compared to Baseline [higher value means less stiffness; less rigidity] |
|---|---|---|
| Tube 1: Smooth Tube (Baseline) | 0.006 | 1.0X |
| Tube 2: 2-rib (load applied inline with ribs) (0.035" rib) | 0.016 | 2.7X |
| Tube 3: 2-rib (load applied off-ribs) | 0.127 | 21.2X |
| Tube 4: 3-rib (.013" rib) | 0.029 | 4.8X |
| Tube 5: 3-rib (.026" rib) | 0.022 | 3.7X |
| Tube 6: 3-rib (.035" rib) | 0.02 | 3.3X |
| Tube 7: 3-rib (.035" rib)( .0568" pitch, thread termination at rib) | 0.018 | 3.0X |
| Tube 8: 3-rib (.040" rib) | 0.017 | 2.8X |
| Tube 9: 3-rib (.050" rib) | 0.015 | 2.5X |
| Tube 10: Zero-rib (continuous thread w/o interruption) | 0.115 | 19.2X |

The finite element analysis for the data compiled with respect to Table 1 above included the following inputs for relative deflections: Model—simplified 1" length (from the distal end of the outer tube); Material—305 SS; Constraints—fully constrained bottom proximal face of 1" sample length Loads −10 lbf applied normal to tube axis on the distal end face and in-line with the rib.

With reference to Table 2 below, the following data was also compiled using finite element analysis to compare tip deflection and max stress of different outer tube designs.

TABLE 2

| Tubes | Distal Tip Deflection (in) | Max Stress (ksi) |
|---|---|---|
| Tube A: Smooth Tube (Baseline) | .110 | 437 |
| Tube B: 3-rib (.030" rib) with circular retention feature | .310 | 992 |
| Tube C: 3-rib (.030" rib) with interrupted circular retention feature | .262 | 807 |
| Tube D: 3-rib (.040" rib) with interrupted circular retention feature | .227 | 646 |

TABLE 2-continued

| Tubes | Distal Tip Deflection (in) | Max Stress (ksi) |
|---|---|---|
| Tube E:<br>3-rib (.050" rib) with interrupted circular retention feature | .202 | 602 |
| Tube F:<br>3-rib (.035" rib) with no retention feature | .307 | 1101 |

The finite element analysis for the data compiled with respect to Table 2 above included the following inputs for relative deflections: Model—full-length production style tube that includes typical production features (e.g., holes, cuts, etc.) that exist for purposes such as attachment to device 230, assembly of shipping wedge, etc.; Material—301 SS; Constraints—fully constrained volume regions were created in the proximal end of the tube to represent the actual contact areas when the tube 300 is assembled on the device 200. Loads –10 lbf applied normal to tube axis on the distal end face and in-line with the rib.

As can be appreciated, securement of any of the components of the presently disclosed devices can be effectuated using known fastening techniques such welding, crimping, gluing, etc.

In accordance with the present disclosure, a kit may be provided including a tack applier 200, an end effector 300, and a set of instructions for using tack applier 200 in combination with end effector 300. In another embodiment, the kit may include at least one tack applier 200, a plurality of end effectors 300, and a set of instructions for using a tack applier 200 in combination with at least one of the plurality of end effectors 300.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 13:
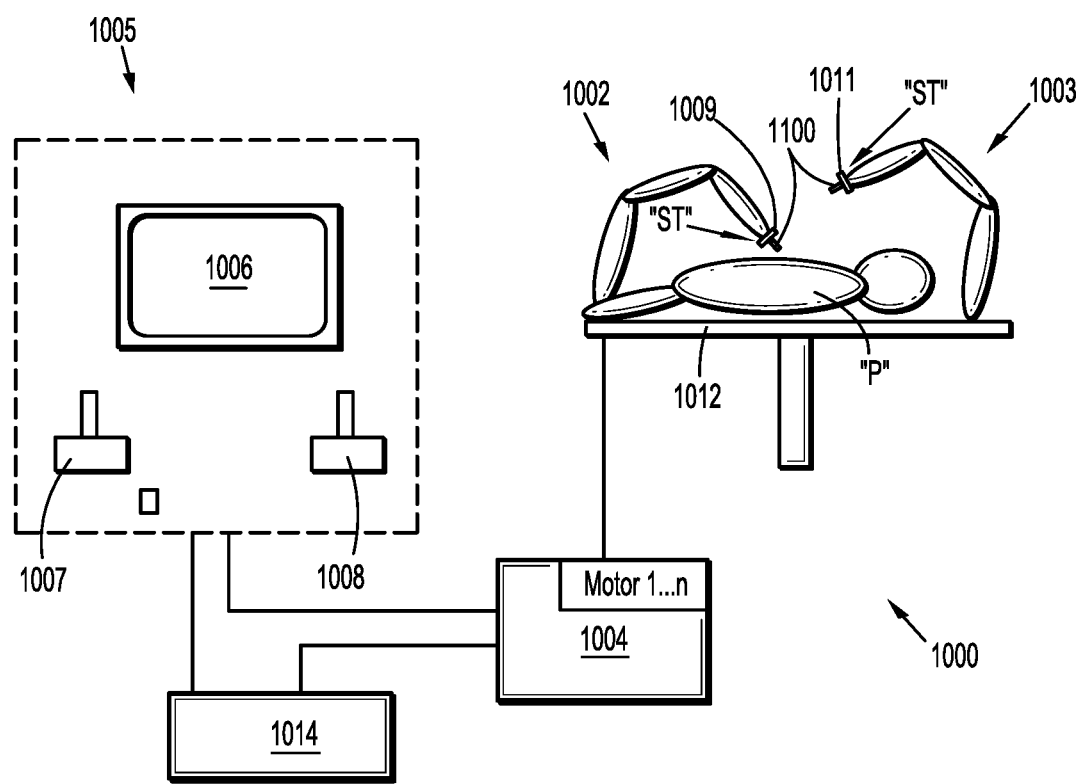
FIG. 13 is a schematic illustration of a medical work station and operating console in accordance with the present disclosure.

Referring also to FIG. 13, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members) in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A surgical system, such as the presently disclosed surgical system, may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A surgical fastening device, comprising:
   a handle;
   a shaft extending from the handle; and
   an end effector supported on the shaft and configured to support at least one fastener, the end effector including:
      a tube defining a longitudinal axis and including an outer surface and an inner surface, the inner surface defining a lumen that extends along the longitudinal axis, the tube defining a proximal depression and a plurality of distal depressions, the proximal depression defined by segments having the same longitudinal alignment, the plurality of distal depressions arranged helically about the inner surface of the tube along the longitudinal axis to guide the at least one fastener through the lumen, the tube defining a tube length; and
      at least one rib continually extending in a plane substantially parallel to the longitudinal axis of the tube, the at least one rib extending continually along a length of the tube length, the length of the tube length defined by at least three of the depressions.

2. The surgical fastening device of claim 1, wherein at least one depression of the plurality of distal depressions is defined by recesses in the outer surface of the tube.

3. The surgical fastening device of claim 2, wherein at least a portion of the depressions of the plurality of distal depressions form grooves at predetermined locations along the tube.

4. The surgical fastening device of claim 3, wherein the grooves are disposed between inner ridges configured to contact the at least one fastener as the at least one fastener advances through the lumen.

5. The surgical fastening device of claim 1, further comprising a drive member supported within the tube, the drive member rotatable relative to the tube to distally advance the at least one fastener along the tube.

6. The surgical fastening device of claim 1, wherein the at least one rib interrupts adjacent depressions of the plurality of distal depressions along the tube.

7. The surgical fastening device of claim 6, wherein the at least one rib includes a plurality of ribs positioned along the tube at predetermined radial locations about the tube to increase stiffness of the tube.

8. The surgical fastening device of claim 7, wherein the plurality of ribs includes three ribs.

9. The surgical fastening device of claim 1, wherein at least some of the plurality of distal depressions are stamped in the tube.

10. An end effector comprising:
    a tube defining a longitudinal axis and including an outer surface and an inner surface, the inner surface defining a lumen that extends along the longitudinal axis and including a proximal inner ridge and distal inner ridges to guide at least one fastener through the lumen, the proximal inner ridge defined by segments disposed in longitudinal alignment with one another, the distal inner ridges disposed in a helical arrangement along the longitudinal axis and having an interrupted pattern, the tube defining a tube length; and
    at least one rib continually extending in a plane substantially parallel to the longitudinal axis of the tube, the at least one rib extending continually along a length of the tube length, the length of the tube length defined by at least three of the inner ridges.

11. The end effector of claim 10, wherein the proximal and distal inner ridges are formed by depressions defined in the outer surface of the tube.

12. The end effector of claim 10, further comprising a drive member supported within the tube, the drive member rotatable relative to the tube to distally advance the at least one fastener along the tube.

13. The end effector of claim 10, wherein the at least one rib extends longitudinally along the outer surface of the tube, the at least one rib creating the interrupted pattern by interrupting adjacent ridges of the proximal or distal ridges.

14. The end effector of claim 13, wherein the at least one rib includes a plurality of ribs supported at spaced apart locations around the tube.

15. An end effector for a surgical fastening device, the end effector comprising:
    a tube defining a longitudinal axis and including an outer surface and an inner surface, the inner surface defining a lumen that extends along the longitudinal axis, the inner surface of the tube defining a proximal depression and a plurality of distal depressions arranged about the tube along the longitudinal axis, the proximal depression defined by segments disposed at the same longitudinal location along the longitudinal axis, the proximal depressions configured to prevent proximal movement of a fastener through the lumen and at least one depression of the plurality of distal depressions configured to facilitate distal advancement of the fastener through the lumen, the tube defining a tube length; and
    at least one rib continually extending in a plane substantially parallel to the longitudinal axis of the tube, the at least one rib extending continually along a length of the tube length, the length of the tube length defined by at least three depressions of the plurality of distal depressions.

16. The end effector of claim 15, wherein at least some depressions of the plurality of distal depressions are defined by recesses in the outer surface of the tube.

17. The end effector of claim 16, wherein the plurality of distal depressions form inner grooves at predetermined locations along the inner surface of the tube.

18. The end effector of claim 15, wherein the tube includes a proximal portion and a distal portion, the proximal portion having a first thickness and the distal portion having a second thickness, the first and second thicknesses being different.

19. The end effector of claim 15, wherein at least one of the proximal depression or one depression of the plurality of distal depressions is stamped in the tube.

\* \* \* \* \*